(12) United States Patent
Williams et al.

(10) Patent No.: US 7,416,305 B2
(45) Date of Patent: *Aug. 26, 2008

(54) METHOD AND APPARATUS FOR IMPROVING VISION AND THE RESOLUTION OF RETINAL IMAGES

(75) Inventors: David R. Williams, Rochester, NY (US); Junzhong Liang, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/199,174

(22) Filed: Aug. 9, 2005

(65) Prior Publication Data

US 2006/0044510 A1 Mar. 2, 2006

Related U.S. Application Data

(63) Continuation of application No. 10/078,163, filed on Feb. 20, 2002, now Pat. No. 6,948,818, which is a continuation of application No. 09/628,690, filed on Jul. 28, 2000, now Pat. No. 6,379,005, which is a continuation of application No. 09/346,309, filed on Jul. 2, 1999, now Pat. No. 6,095,651, which is a continuation of application No. 09/071,794, filed on May 4, 1998, now Pat. No. 5,949,521, which is a continuation of application No. 08/772,977, filed on Dec. 23, 1996, now Pat. No. 5,777,719.

(51) Int. Cl.
*A61B 3/10* (2006.01)

(52) U.S. Cl. ...................................................... 351/221

(58) Field of Classification Search ................. 351/200, 351/205–207, 211, 212, 215, 221, 246, 247, 351/160, 177, 160 R; 623/6.11; 606/4–6, 606/10–12; 600/558; 604/289; 607/53–54; 359/846–849

See application file for complete search history.

(56) References Cited

U.S. PATENT DOCUMENTS

| | | | |
|---|---|---|---|
| 4,523,821 A | 6/1985 | Lang et al. |
| 4,632,528 A | 12/1986 | Yoshino et al. |
| 4,721,379 A | 1/1988 | L'Esperance |
| 4,764,930 A | 8/1988 | Bille et al. |
| 4,838,679 A | 6/1989 | Bille |
| 4,848,340 A | 7/1989 | Bille et al. |
| 4,881,808 A | 11/1989 | Bille et al. |
| 4,991,953 A | 2/1991 | Pflibsen et al. |
| 5,062,702 A | 11/1991 | Bille |
| 5,098,426 A | 3/1992 | Sklar et al. |
| 5,114,628 A | 5/1992 | Hofer et al. |
| 5,139,022 A | 8/1992 | Lempert |
| 5,159,361 A | 10/1992 | Cambier et al. |
| 5,173,723 A | 12/1992 | Volk |
| 5,177,511 A | 1/1993 | Feuerstein et al. |
| 5,184,157 A | 2/1993 | Ichihashi et al. |
| 5,198,845 A | 3/1993 | Triller |
| 5,202,709 A | 4/1993 | Ichihashi et al. |
| 5,214,456 A | 5/1993 | Gersten |
| 5,229,889 A | 7/1993 | Kittell |
| 5,233,174 A | 8/1993 | Zmek |
| 5,243,367 A | 9/1993 | Spellitz |
| 5,258,791 A | 11/1993 | Penney et al. |
| 5,293,871 A | 3/1994 | Reinstein et al. |
| 5,307,097 A | 4/1994 | Baker |
| 5,404,884 A | 4/1995 | Lempert |
| 5,418,714 A | 5/1995 | Sarver |
| 5,442,412 A | 8/1995 | Frey et al. |
| 5,452,031 A | 9/1995 | Ducharme |
| 5,473,392 A | 12/1995 | Klopotek |
| 5,474,548 A | 12/1995 | Knopp et al. |
| 5,475,452 A | 12/1995 | Kuhn et al. |
| 5,490,849 A | 2/1996 | Smith |

| | | | |
|---|---|---|---|
| 5,491,524 A | 2/1996 | Hellmuth et al. |
| 5,493,391 A | 2/1996 | Neal et al. |
| 5,502,518 A | 3/1996 | Lieberman |
| 5,512,965 A | 4/1996 | Snook |
| 5,512,966 A | 4/1996 | Snook |
| 5,548,354 A | 8/1996 | Kasahara et al. |
| 5,549,632 A | 8/1996 | Lai |
| 5,570,142 A | 10/1996 | Lieberman |
| 5,581,347 A | 12/1996 | Le Saux et al. |
| 5,592,246 A | 1/1997 | Kuhn et al. |
| 5,629,765 A | 5/1997 | Schmutz |
| 5,632,742 A | 5/1997 | Frey et al. |
| 5,722,427 A | 3/1998 | Wakil et al. |
| 5,735,283 A | 4/1998 | Snook |
| 5,740,803 A | 4/1998 | Gray et al. |
| 5,777,719 A | 7/1998 | Williams et al. |
| 5,784,146 A | 7/1998 | Nanjo et al. |
| 5,822,035 A | 10/1998 | Bille |
| 5,841,511 A | 11/1998 | D'Souza et al. |
| 5,847,804 A | 12/1998 | Sarver et al. |
| 5,861,955 A | 1/1999 | Gordon |
| 5,949,521 A | 9/1999 | Williams et al. |
| 6,002,484 A | 12/1999 | Rozema et al. |
| 6,241,355 B1 | 6/2001 | Barsky |
| 6,267,756 B1 | 7/2001 | Feuerstein et al. |
| 6,271,914 B1 | 8/2001 | Frey et al. |
| 6,271,915 B1 | 8/2001 | Frey et al. |

FOREIGN PATENT DOCUMENTS

| | | |
|---|---|---|
| DE | 42 22 395 | 1/1994 |
| EP | 0 329 981 A1 | 8/1989 |
| JP | 05-146409 | 6/1993 |
| JP | 61-71032 | 6/1994 |
| JP | 06-327634 | 11/1994 |
| JP | 63-11130 | 11/1994 |
| WO | WO-87/05204 | 9/1987 |
| WO | WO 87/05205 | 9/1987 |
| WO | WO-87/05205 | 9/1987 |
| WO | WO-90/09141 | 8/1990 |
| WO | WO 92/01417 | 2/1992 |
| WO | WO-95/13012 | 5/1995 |
| WO | WO 95/28989 | 11/1995 |
| WO | WO 98/27863 | 7/1998 |

OTHER PUBLICATIONS

"Basic Wavefront Aberration Theory for Optical Metrology", J. Wyant, Chatper 1, Academic Press, 1992, ISBN 0-12-408611-X.
C. Labjuhn, et al., Astigmatismuskorrektur durch Laserthermokeratoplastik (LTK)—Ein Ansatz für die Korrektur des hohen Astigmatismus nach Perforierender Keratoplastik, Contactologia 18 D (1996).
Cohen, Kenneth, et al., Assessment of the Power and Height of Radial Aspheres Reported by a Computer-assisted Keratoscope, American Journal of Ophthalmology, vol. 19, No. 6, Nov. 30, 1994, pp. 723-732.
Corbett, Melanie C., et al., The Topography of Normal Cornea, Eur J. Implant Ref Surg., vol. 6, Oct. 1994, pp. 296-297.
Maeder, Anthony J., et al., Accurate 3D Corneal Surface Measurement Using An Automated Mapping Approach, Mar. 1995, pp. 328-334.
Salmon, Thomas O., et al., Comparison of Elevation, Curvature, and Power Descriptors for Corneal Topographic Mapping, 1995, pp. 800-808.
Pavlopoulos, Georgios, P., et al., The Effect of Artifical Tears on Computer-Assisted Corneal Topography in Normal Eyes and After Penetrating KeratoplaSty, Jun. 1995, pp. 712-722.
Roberts, Cynthia, Characterization of the Inherent Error in a Spherically-Biased Corneal Topography System in Mapping a Radially Aspheric Surface3, Mar./Apr. 1994, pp. 103-111.
Thornton, Spencer P., Clinical Evaluation of Corneal Topography, 1993, pp. 198-202.
Wilson, Steven, et al., Accuracy and Precision of the Corneal Analysis System and the Topographic Modeling System, 1992, pp. 28-35.

Bogan, Stephen J., et al., Computer-Assisted Videokeratography of Corneal Topography After Radial Keratotomy, Jun. 1991, pp. 834-841.
Bogan, Stephen J., et al., Classification of Normal Corneal Topography Based on Computer-Assisted Videokeratography, Jul. 1990, pp. 945-949.
Reidy, James J., et al., The Corneal Topography of Normal Corneas, Apr. 1989, pp. 512-518.
Rabompwotz. Yaron S., et al., Computer-Assisted Corneal Topography in Keratoconus, Nov./Dec. 1989, pp. 400-408.
Dingeldein, Steven A., et al., The Topography of Normal Corneas, Apr. 1989, pp. 512-518.
Rabinowitz, Yaron S., et al., Computer-Assisted Corneal Topography in Keratoconus, Nov./Dec. 1989, pp. 400-408.
McDonnell, Peter J., et al., Topographic Analysis and Visual Acuity After Radial Keratotomy, Dec. 1989, pp. 692-695.
McDonnell, Peter J., et al., Corneal Topographic Changes After Radial Keratotomy, Jan. 1989, pp. 45-49.
Kiely, P.M., e tal., The mean shape of the human cornea, 1982, pp. 1027-1040.
Liang, et al., Objective measurement of wave aberrations of the human eye with the use of a Hartmann wave-front sensor, Journal Optical Society of America, Jul. 1994, vol. 11, No. 7, pp. 1-9.
Walsh, et al., Objective technique for the determination of monochromatic aberrations of the human eye, Journal Optical Society of America, Sep. 1984, vol. 1, No. 9, pp. 987-992.
Charman, W., Wavefront Aberration of the Eye: a Review, Optometry and Vision Science, American Academy of Optometry, vol. 68, No. 8, opp. 574-583.
Bartsch, et al., Resolution Improvement of Confocal Scanning Laser Tomography of Human Fundus, Retin Imagining Laboratory, Shiley Eye Center-Department of Opthalmology, University of California San Diego, pp. 134-137.
Dreher, et al., Active optical depth resolution improvement of laser tomographic scanner, Applied Optics, Feb. 15, 1989, vol. 28, No. 4, pp. 804-808.
Bille, et al., Scanning Laser Tomography of the Living Human Eye, Chapter 28, pp. 528-547.
H. Howland et al, "Research Note: Computing High Order Wave Aberration Coefficients from Variations of Best Focus for Small Artificial Pupils," *Vision Res.* vol. 29, No. 8, pp. 979-983, 1989.
Liang et al, "New Objective Measurements of the Wave Aberrations of the Human Eye," *ARVO Investigative Ophthalmology & Visual Science Abstract Book*, Annual Meeting, Fort Lauderdale, Florida, May 14-19, 1995, p. S188.
Liang et al, "Effect of Higher Order Aberrations on Image Quality of the Human Eye," *Technical Digest: Vision Science and Its Applications*, 1995 Topical Meeting on Visual Science and Its Application, Santa Fe, New Mexico, Feb. 3-7, 1995, pp. 70-73.
Liang, *A New Method to Precisely Measure the Wave Aberrations of the Human Eye with a Hartmann-Shack-Wavefront-Sensor: Inaugural-Dissertation zur Erlangung der Doktorwürde der Naturwissenschaftlich-Mathematischen Gesamtfakultät der Ruprecht-Karls-Universität Heidelberg*, doctoral thesis presented at the University of Heidelberg, Dec. 1991.
Webb et al, "Measurement of Local Refractive Error," *Noninvasive Assessment of the Visual System: 1991 Technical Digest Series vol. 1*, Noninvasive Assessment of the Visual System Topical Meeting, Santa Fe, New Mexico, Feb. 4-7, 1991, pp. 230-233.
Webb, "Zernike polynomial description of ophthalmic surfaces," *Ophthalmic and Visual Optics: 1992 Technical Digest*, vol. 3, Santa Fe, New Mexico, Jan. 28-30, 1992, pp. 38-41.
Webb et al, "Measurement of ocular local wavefront distortion with a spatially resolved refractometer," *Applied Optics*, vol. 31, No. 19, Jul. 1, 1992, pp. 3678-3686.
Jason Porter, "Measuring the Wave Aberration of the Human Eye with a Hartmann-Shack Wavefront Sensor," *Center for Visual Science University of Rochester* Apr. 30, 1997.
James C. Wyant et al, *Applied Optics and Optical Engineering*, vol. XI, "Chapter 1: Basic Wavefront Aberration Theory for Optical Metrology," © Academic Press, ISBN 0-12-408611-X, pp. 1 and 28-39.
M.S. Smirnov, "Measurement of the Wave Aberrartion of the Human Eye," *Biofizika* 6: No. 6, 687-703, 1961.
H. Howland et al, "A subjective method for the measurement of monochromatic aberrations of the eye," *J. Opt. Soc. Am.*, vol. 11, Nov. 1977, pp. 1508-1517.

G. Walsh et al, "Objective technique for the determination of monochromatic aberrations of the human eye," *J. Opt. Soc Am. A*, vol. 1, No. 9, Sep. 1984, pp. 987-992.

G. Walsh et al, "Measurement of the Axial Wavefront Aberration of the Human Eye," *Ophthal. Physiol. Opt.*, vol. 5, No. 1, pp. 23-31, 1985.

*Primary Examiner*—George Manuel
(74) *Attorney, Agent, or Firm*—Blank Rome LLP

(57) ABSTRACT

A method of and apparatus for improving vision and the resolution of retinal images is described in which a point source produced on the retina of a living eye by a laser beam is reflected from the retina and received at a lenslet array of a Hartmann-Shack wavefront sensor such that each of the lenslets in the lenslet array forms an aerial image of the retinal point source on a CCD camera located adjacent to the lenslet array. The output signal from the CCD camera is acquired by a computer which processes the signal and produces a correction signal which may be used to control a compensating optical or wavefront compensation device such as a deformable mirror. It may also be used to fabricate a contact lens or intraocular lens, or to guide a surgical procedure to correct the aberrations of the eye. Any of these methods could correct aberrations beyond defocus and astigmatism, allowing improved vision and improved imaging of the inside of the eye.

10 Claims, 3 Drawing Sheets

FIG. 3a WITHOUT COMPENSATION

FIG. 3b WITH COMPENSATION

METHOD AND APPARATUS FOR IMPROVING VISION AND THE RESOLUTION OF RETINAL IMAGES

REFERENCE TO RELATED APPLICATION

The present application is a continuation of U.S. patent application Ser. No. 10/078,163 filed Feb. 20, 2002 now U.S. Pat. No. 6,948,818, now pending, which is a continuation of U.S. patent application Ser. No. 09/628,690, filed Jul. 28, 2000, now U.S. Pat. No. 6,379,005, which is a continuation of U.S. patent application Ser. No. 09/346,309, filed Jul. 2, 1999, now U.S. Pat. No. 6,095,651, which is a continuation of U.S. patent application Ser. No. 09/071,794, filed May 4, 1998, now U.S. Pat. No. 5,949,521, which is a continuation of U.S. patent application Ser. No. 08/772,977, filed Dec. 23, 1996, now U.S. Pat. No. 5,777,719. The disclosure of all of the above applications are hereby incorporated by reference in their entireties.

BACKGROUND OF THE INVENTION

The present invention is directed to a method of and an apparatus for improving vision and the resolution of retinal images. More particularly, the present invention is directed to a method of and an apparatus for measuring and correcting the wave aberration of the eye such that the measured data can be used to develop corrective optical elements for improving the optical quality of the eye.

Despite significant advances in spectacle and contact lens design, current ophthalmic lenses still can only correct defocus and astigmatism. Spectacles and contact lenses leave uncorrected additional aberrations such as spherical aberration, coma, and a host irregular aberrations. These high order aberrations of the eye not only blur images formed on the retina, which impairs vision, but also blur images taken of the living human retina. There have been two obstacles that prevent the use of specially-designed optical elements to correct aberrations beyond defocus and astigmatism in the eye. First, quantitative measurement of the irregular aberrations of the eye has not been possible. Second, a mechanism to correct the monochromatic aberrations of the eye other than defocus and astigmatism has not been demonstrated.

Subjective refractive methods of optometrists and objective autorefractors measure defocus and astigmatism only. They cannot measure the complete wave aberration of the eye, which includes all aberrations left uncorrected by conventional spectacles. The objective aberroscope disclosed by Walsh et al. in the Journal of the Optical Society of America A, Vol. 1, pp. 987-992 (1984) provides simultaneous wave aberration measurement of the entire pupil but cannot sample the pupil with a spacing finer than about 0.9 mm (See Charman in Optometry and Vision Science, Vol. 68, pp. 574-583 (1991)). Moreover, rapid, automated computation of the wave aberration has not been demonstrated with this method.

Recently, one of the co-inventors herein, together with others, developed an apparatus to measure the wave aberration of the eye. In a report entitle "Objective measurement of wave aberration of the human eye with the use of a Hartmann-Shack wave-front sensor", Liang et al., J. Opt. Soc. Am. A., volume 11, number 7, pp. 1-9, July 1994, the disclosure of which is incorporated by reference herein, the authors disclosed a Hartmann-Shack wavefront sensor that they used to measure the wave aberrations of the human eye by sensing the wavefront emerging from the eye produced by the retinal reflection of a focused light beam on the fovea. Using the system disclosed therein, the authors were able to measure only up to fourth order polynomial functions. The wavefront fitting with polynomials up to fourth order does not provide a complete description of the eye's aberrations. That description is generally insufficient to accurately compute the optical performance of the eye. This instrument was not equipped to remove unwanted light reflected from other surfaces, such as lenses and the cornea of the eye.

There has also been a previous attempt to correct the monochromatic aberrations of the eye beyond defocus and astigmatism, with the goal of improving the axial resolution of the confocal scanning laser ophthalmoscope. Bartsch et al., in Vision Science and its Applications, 1994, *Technical Digest Series*, Vol. 2 (Optical Society of America, Washington, D.C.) pp. 134-137 (1994) used a fundus contact lens to null the refraction at the first surface of the cornea. That approach, however, suffers from the fundamental problem that the wave aberration of the eye depends on the combined effects of refractive index variations throughout the eye's optics. Possibly for that reason, an attempt to use a fundus contact lens to increase the axial resolution of a confocal scanning laser ophthalmoscope showed only modest improvement.

Another approach is to use a deformable mirror, a device that has successfully compensated for atmospheric turbulence in ground-based telescope. A deformable mirror was previously proposed for use in a confocal laser scanning ophthalmoscope in conjunction with the human eye in U.S. Pat. No. 4,838,679 to Billie, but no method to measure the wave aberration of the eye was proposed or disclosed. Dreher, Bille, and Weinreb, in Applied Optics, Vol. 28, pp. 804-808 demonstrated the only usage of a deformable mirror for the eye, but only corrected the astigmatism of the eye, which is no better than the correction provided by conventional ophthalmic lenses. The use of an optical element to correct monochromatic aberrations higher than second order has never been achieved. In both those systems, no appropriate method for measuring the eye's high order aberrations was disclosed. Bille et al., in Noninvasive Diagnostic Techniques in Ophthalmology, edited by Masters, B. R., Springer-Verlag, pp. 528-547 (1990) proposed the use of a wavefront sensor in conjunction with a deformable mirror, but a working system was never disclosed or realized.

SUMMARY AND OBJECTS OF THE INVENTION

In view of the foregoing, it is apparent that there exists a need in the art for a method of and an apparatus for producing ophthalmic optical elements that provide improved or supernormal vision over that which is currently available, as well as high resolution retinal images. It is, therefore, a primary object of the present invention to provide a method of and an apparatus for accurately measuring higher order aberrations of the eye and for using the data thus measured to compensate for those aberrations with a customized optical element.

It is also an object of the present invention to provide an improved wavefront sensor which rejects light reflected from structures other than the retina and which is capable of providing a complete measurement of the eye's aberrations.

It is a further object of the present invention to utilize such an improved wavefront sensor in combination with a deformable mirror to correct the wave aberration in a feedback manner such that the subject achieves normal or supernormal vision.

It is likewise a primary object of the present invention to provide a method of and an apparatus for producing high resolution retinal images which allow the imaging of microscopic structures the size of single cells in a human retina.

Briefly described, these and other objects of the invention are accomplished by providing a system for receiving light reflected from a retina of an eye. The wavefront in the plane of the pupil is recreated in the plane of a lenslet array of a Hartmann-Shack wavefront sensor. Each of the lenslets in the lenslet array is used to form an aerial image of the retinal point source on a CCD camera located adjacent to the lenslet array. The wave aberration of the eye, in the form of a point source produced on the retina by a laser beam, displaces each spot by an amount proportional to the local slope of the wavefront at each of the lenslets. The output from the digital CCD camera is sent to a computer which then calculates the wave aberration and provides a signal to a deformable mirror. Following an iterative procedure, the deformable mirror ultimately acquires a shape that is identical to the wave aberration measured at the outset, but with half the amplitude. This deformation is the appropriate one to flatten the distorted wavefront into a plane wave, which improves image quality.

In its method aspects, the system of the present invention, using the computer, first acquires the CCD image, as described above. Then, the computer computes the centroid of the spot formed by each of the lenslets of the wavefront sensor. Shifts in each focus spot in the x and y directions are calculated and then used as the slope data to fit with the sum of the first derivatives of 65 Zernike polynomials, using a least squares procedure, to determine the weight for each polynomial.

Then, the Zernike polynomials are weighted with the calculated coefficients. The 65 polynomials in the wavefront fit include all Zernike modes with radial power less than or equal to 10, except for the piston term.

The weighted Zernike polynomials are then added together, to result in the reconstructed wave aberration. The wave aberration is then evaluated at the locations of the actuators of a deformable mirror in order to produce the correction signal which is sent by the computer to the wavefront compensation device or deformable mirror, as discussed above. Such a feedback loop continues to receive the reconstructed wave aberration results, feeding back an appropriate correction signal, until the RMS of the reconstructed wave aberration signal reaches an asymptotic value, at which point, the deformable mirror has been deformed such that it will compensate for all the detected aberrations of the eye.

When the reconstructed wave aberration signal reaches its asymptotic value, the final aberration signal (including all of the previously generated signals up until the RMS error reaches the asymptotic value) can be used to produce contact lenses to correct for all of the monochromatic aberrations of the human eye or for surgical procedures.

The present invention can also be used to provide high resolution images of the retina The system for producing such images uses a krypton flash lamp which is designed to illuminate a retinal disk to provide an image of the retina which is reflected by the deformable mirror onto a lens and through an aperture such that the reflected image of the retina is focused onto a second CCD camera. The signals generated by the camera are acquired in a manner similar to that described above in connection with the first CCD camera and are stored for later use in the computer.

With these and other objects, advantages, and features of the invention that may become hereinafter apparent, the nature of the invention may be more clearly understood by reference to the following detailed description of the invention, the appended claims and to the drawings attached herein.

BRIEF DESCRIPTION OF THE DRAWINGS

FIGS. 3a-3d show the wave aberration and the corresponding point spread functions before and after adaptive compensation using the system of the present invention, respectively; and, FIG. 4 shows the Zernike decomposition of the wave aberration of the eye before and after adaptive compensation, showing that the invention can correct not only second order aberrations (defocus and astigmatism) but also high-order aberrations.

DETAILED DESCRIPTION OF THE PREFERRED EMBODIMENT

Figure 1:
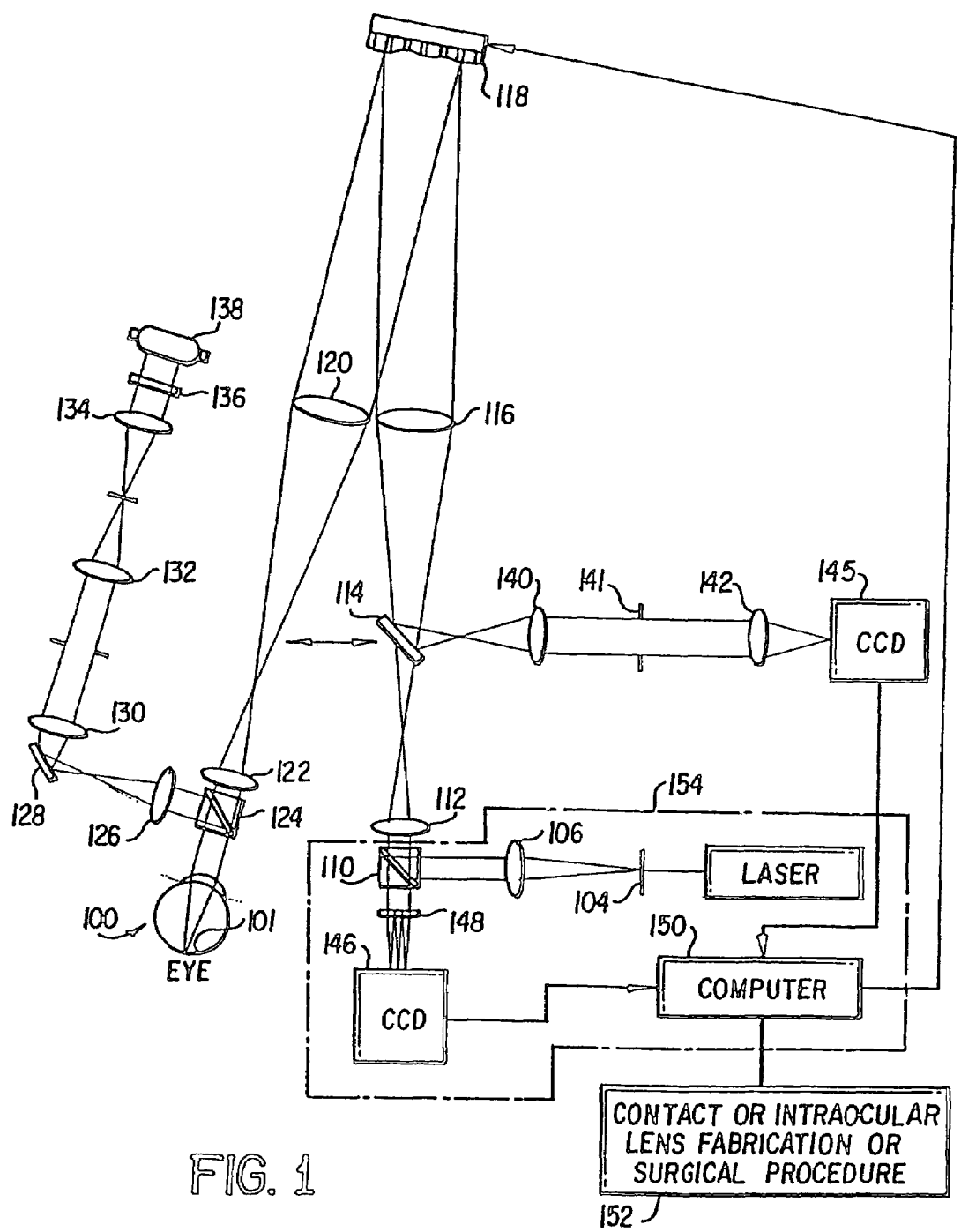
FIG. 1 is a schematic diagram of the system of the present invention.

Referring now to FIG. 1, there is shown, in schematic diagram form, the apparatus of the present invention which can be used to both improve visual performance and to provide high resolution retinal images of eyes. The apparatus of the present invention, as shown in FIG. 1, measures the aberrations of the eye using a Hartmann-Shack wavefront sensor and then corrects them in a closed feedback loop with a compensating optical component such as a deformable mirror.

To measure the eye's wave aberration, a point source is produced on the retina by a laser 102. The light from the laser 102, is controlled by a shutter (not shown). The laser light passes through a spatial filter 104 and is collimated by an achromatic doublet lens 106. The collimated laser beam is reflected by the polarizing beamsplitter 110, passes through the lenses 112 and 116, and is incident onto a deformable mirror 118. The laser beam reflected from the deformable mirror 118 is focused by the lens 120, passes through the lens 122 and the second beamsplitter 124 and reaches the eye 100 at a diameter of about 1.5 mm at the pupil. The lens of the eye 100 focuses the laser beam on its retina 101. Possible myopia or hyperopia of the tested eye is corrected by movement of the eye 100 and the lens 122 with respect to the lens 120.

The light reflected from the retina 101 forms a distorted wavefront at the pupil, which is recreated in the plane of the deformable mirror 118 by the lenses 122 and 120, and also in the plane of the lenslet array of a Hartmann-Shack wavefront sensor 148 by the lenses 116 and 112. The pupil is conjugate with a two-dimensional array of lenslets 148. Each of the lenslets in the array 148 forms an aerial image of the retinal point source on the CCD camera 146. The CCD camera 146 sends the digitized image to the computer 150 where it is stored in RAM or on magnetic or other storage media.

Aberrations displace each spot by an amount proportional to the local slope of the wavefront at each lenslet. The slope of the wavefront can be determined from the displacement of these spots relative to a known aberration-free reference. The wavefront sensor 154 measures the local slopes in both the x and y directions at 217 locations simultaneously across the dilated pupil. From the array of slopes, the wave aberration is reconstructed as described later herein.

The beamsplitter 110 which forms part of the wavefront sensor 154 is preferably configured as a polarizing beamsplitter in order to remove unwanted light reflected from the first surface of the cornea of the eye 100 and other optical elements, such as lenses 112, 116, 120, and 122. Such light would otherwise interfere with the operation of the wavefront sensor 154 and would make automatic procedures for measuring the wave aberration more difficult.

The wavefront sensor 154 of the present invention provides a much more complete measurement of the aberrations of the eye than has been possible before in part because a large number of samples in the pupil of the eye are used. Using the apparatus of the present invention, it has been found that the eye 100 contains complex aberrations that are not corrected by spectacles or contact lenses, and that such aberrations are significant when the pupil is large. Even aberrations of order 5 and greater, which the present wavefront sensor 154 is the first to measure, has significant impact on the eye's optical quality. Moreover, the higher order aberrations are stable over time. Such stability is important because it shows that the aberrations can be corrected using a static optical corrector, such as a custom-made contact lens.

Once the wave aberration is measured, as described above, it is compensated with a device conjugate with the pupil of the eye 100 that can control the phase of the light at different points in the pupil. As will be further described in detail in connection with FIG. 2, the computer 150, under software control, produces a correction signal which is fed back to the deformable mirror 118. The deformable mirror 118, which is available as model no. RX-170407-C from Xinetics, Inc., is conjugate with the pupil of the eye 100 and will be deformed to compensate for the wave aberration of the eye. The deformable mirror 118 contains an aluminized glass faceplate with 37 actuators mounted in a square array on the back surface. Alternatively, a liquid crystal device, a micro-machined mirror, a bimorph mirror, or other suitable device could be used in place of the deformable mirror 118.

The apparatus of FIG. 1 is used as follows. The computer 150 starts the measurement process by opening the pathway of the laser beam from the laser 102. The light returning from the retina 101 is used to measure the wave aberration. The Hartmann-Shack wavefront sensor 148 provides a measurement of the eye's wave aberration, from which the deformable mirror 118 is driven to correct it. The process is repeated with the computer 150 generating suitable signals to cause the deformable mirror 118 to continue deforming until the RMS error in the measured wave aberration reaches an asymptotic value, although other criteria might be used. At that point, the deformable mirror 118 has taken the appropriate shape to provide wavefront compensation for the aberrations of the eye.

Also at that point, the final correction signal generated by the computer 150 can be provided to a contact lens fabrication system 152 used to fabricate contact lenses which would duplicate the wavefront compensation characteristics of the deformable mirror 118. As would be obvious to those of ordinary skill in the art, such contact lenses would be custom ground for each eye for which compensation is to be provided.

Figure 2:
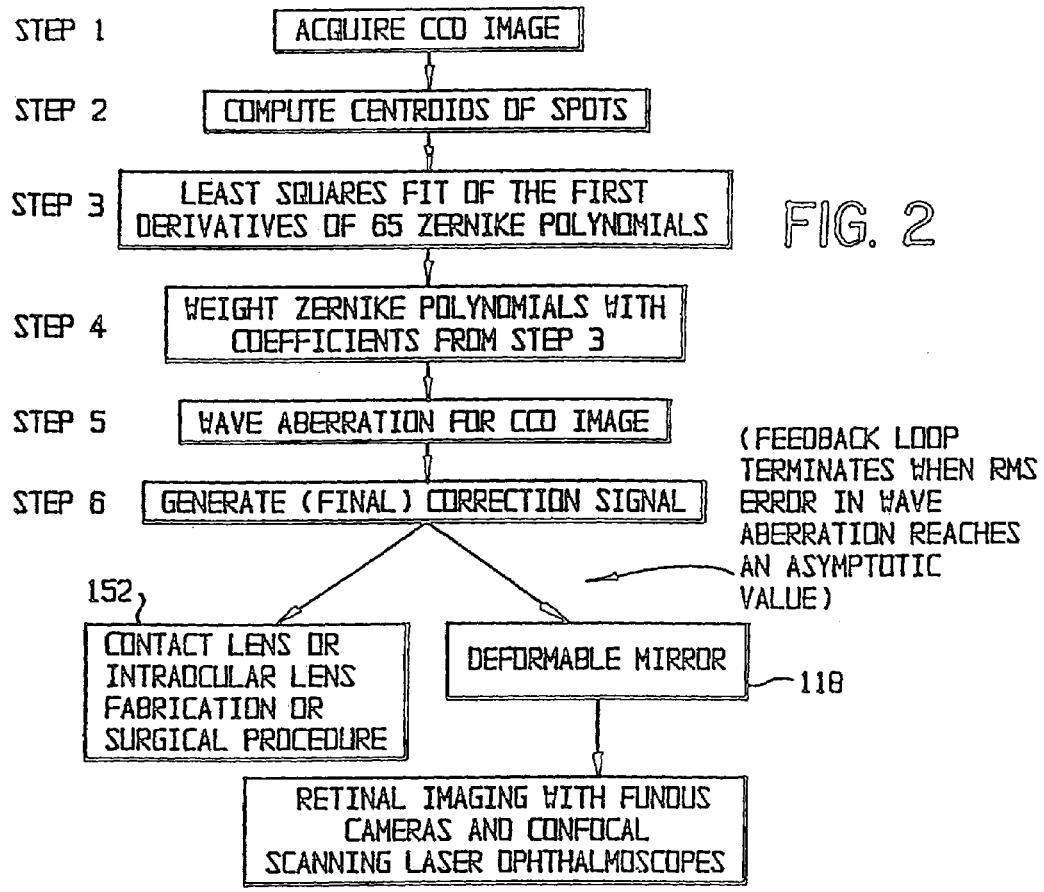
FIG. 2 is a diagram of a flow chart of a method for the present invention for use in fabricating contact lenses or providing retinal images using the apparatus shown in FIG. 1.

Turning now to FIG. 2, there is shown in diagrammatic flow chart form the steps performed by the software resident in the computer 150 for utilizing the data obtained from the CCD device 146. At Step 1, the digital image is acquired by the computer 150 from the CCD camera. Each image consists of 512 pixels by 512 pixels at 12 bits. Then, at Step 2, the computer 150 computes the centroid of the spot formed by each lenslet of the wavefront sensor. The centroid of each spot specifies its position. By comparing the positions of corresponding spots in a reference pattern and in the pattern obtained from the eye, the shifts in each focus spot in both the x and y directions can be calculated.

Next, at Step 3, the slope data are fit with the sum of the first derivatives of 65 Zernike polynomials, using a least squares procedure to determine the weight for each polynomial, similar to that discussed by Liang et al. in their report referenced above, though their method included no polynomials beyond fourth order.

Then, at Step 4, the Zernike polynomials are weighted with the coefficients calculated at Step 3. The 65 polynomials in the wavefront fit include all Zernike modes with radial power less than or equal to 10, except for the piston term. The first order Zernike modes are the linear terms. The second order modes are the quadratic terms, which correspond to the familiar aberrations, defocus, and astigmatism. The third order modes are the cubic terms, which correspond to the coma and coma-like aberrations. The fourth order modes contain spherical aberrations as well as other modes. The fifth to tenth order modes are the higher-order, irregular aberrations. Local irregularities in the wavefront within the pupil are represented by these higher-order Zernike modes.

The weighted Zernike polynomials are added together at Step 5 to obtain the reconstructed wave aberration. The wave aberration is evaluated at the locations of the actuators of the deformable mirror 118 to produce a correction signal at Step 6, which is then sent by the computer 150 to the wavefront compensation device which, as shown in FIG. 1, is preferably a deformable mirror 118. The feedback loop continues to receive the reconstructed wave aberration results, feeding back an appropriate correction signal until the RMS error in the reconstructed wave aberration signal reaches an asymptotic value. At that point, the deformable mirror 118 has been deformed such that, when the eye looks through it, it will compensate for all of the detected aberrations of the eye 100.

As is known to those of ordinary skill in the art, spectacles and contact lenses are available to correct vision, but they only correct defocus and sometimes astigmatism in the eye. Even normal eyes have other aberrations that are not corrected by conventional spectacles or contact lenses. The wavefront sensor 154 of the present invention is capable of automatically measuring those aberrations. Thus, using the adaptive optics system of FIG. 1 allows correction of monochromatic aberrations of the human eye beyond defocus and astigmatism. Accordingly, the adaptive optics system of FIG. 1 provides unprecedented optical quality in human eyes, both for improved vision and for providing sharper pictures of the retina.

Figure 3C:
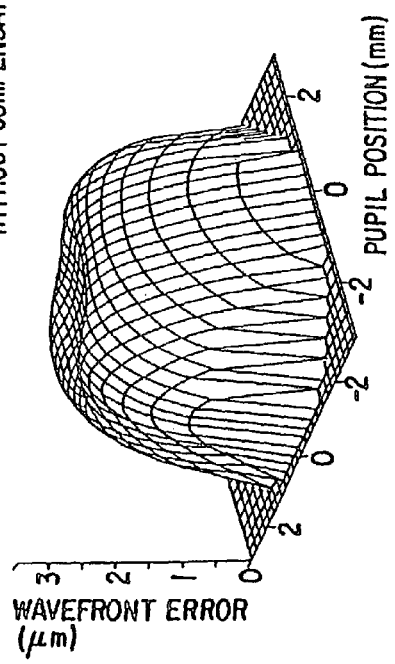
Figure 3C:
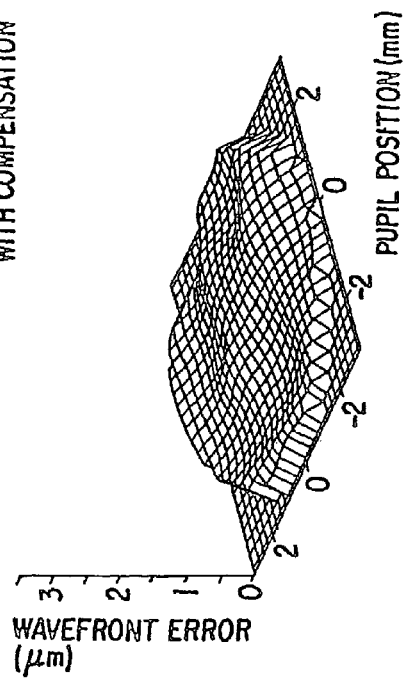
Figure 3C:
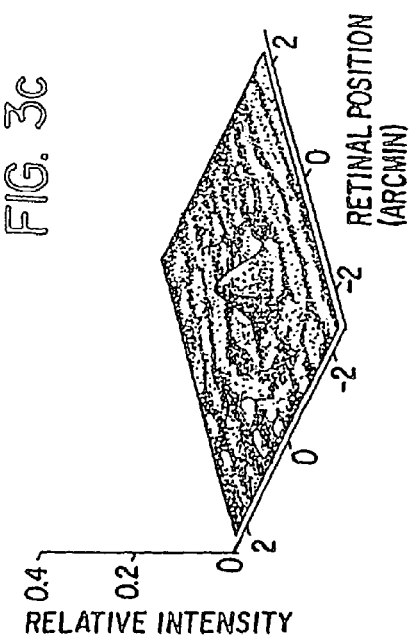

FIGS. 3a-3d are graphs of data from the wavefront sensor showing that the adaptive optics system of the present invention successfully corrects the aberrations of the eye. FIGS. 3a and 3b show, for one subject, the wavefront error versus pupil position without adaptive compensation and with adaptive compensation, respectively, using the present invention. In a test in which four subjects were measured, adaptive compensation reduced the peak to valley wavefront error across a 6 mm pupil by a factor of 4, on average.

Figure 3D:
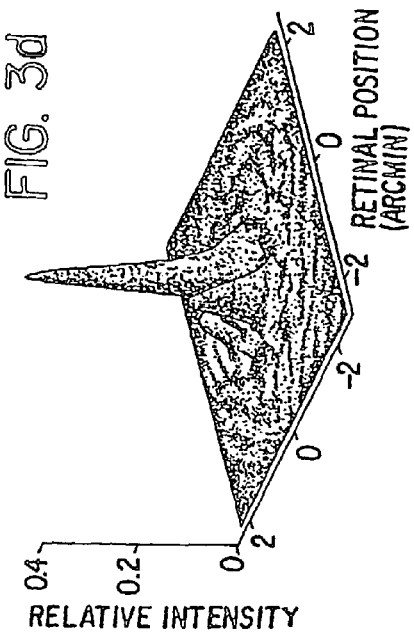

FIGS. 3c and 3d show the point spread function (PSF), computed from the wave aberration, without adaptive compensation and with adaptive compensation, respectively. Adaptive compensation increased the Strehl ratio, which is proportional to the peak intensity of the PSF, from 0.09 to 0.47. The average increase for all four eyes measured was nearly 4 fold, from 0.06 to 0.23. After compensation, the PSF for the subject shown has a full-width at half height (FW of 2.0 microns, close to the value of 1.9 microns expected from diffraction alone. The present invention provides what is believed to be the best optical quality ever achieved in the human eye.

Figure 4:
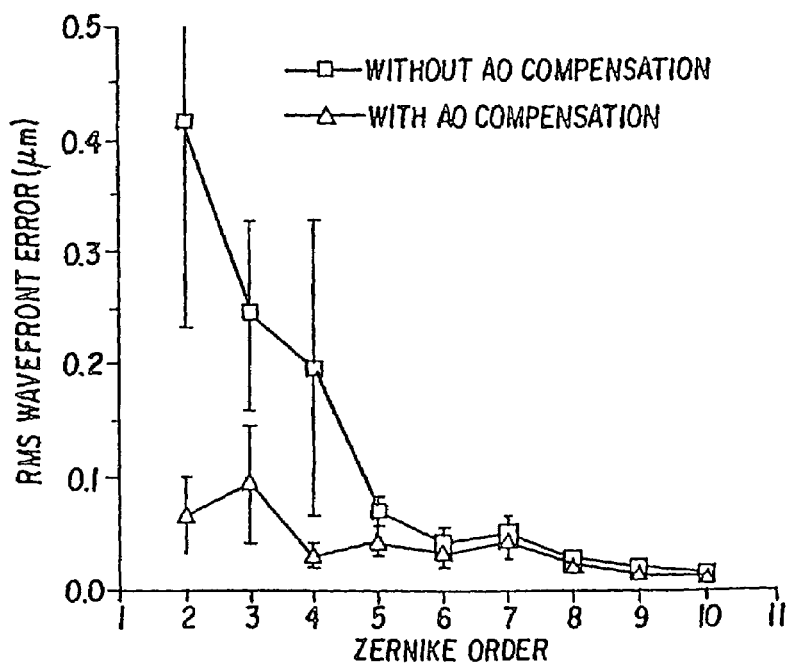

FIG. 4 is a graph of the RMS wavefront error, averaged across 4 eyes, associated with each Zernike order of the wave aberration. The RMS wavefront error is reduced by adaptive compensation for Zernike orders up to fifth order. Spectacles, contact lenses, and one previous attempt to use a deformable mirror to correct the eye's aberrations have only corrected second order aberrations (defocus and astigmatism).

Once the correction has been achieved, the apparatus of the present invention can be used to provide the subject with supernormal retinal image quality, in which case the subject views visual imagery through the deformable mirror 118. A six-fold improvement in vision, as measured with contrast sensitivity for fine gratings, for individuals looking through the present apparatus has been achieved. Individuals can see very high frequency gratings through the adaptive optics system that are above the resolution limit in normal viewing without adaptive optics.

Alternatively, once the correction has been achieved, the apparatus of the present invention shown in FIG. 1 can also be used to provide high resolution images of the retina 101. A krypton flash lamp 138 is imaged onto the eye's pupil by the lenses 134, 132, 130, and 120 after passing through the beamsplitter 124. The lamp 138 delivers a 4 msec flash, thereby illuminating a retinal disk on the retina 101 that is 1 degree in diameter. A narrow band interference filter 136 shapes the spectral output of the lamp 138.

The image of the retina 101 passes through the beamsplitter 124 and the lenses 122 and 120, is reflected by the deformable mirror 118, which has already been shaped to compensate for the eye's aberrations, and passes through the lens 116. The light is then reflected by the mirror 114 onto the lens 140 and through an aperture 141, where the reflected image is focused by the lens 142 onto the CCD device 145. The electrical signals corresponding to the light captured by the CCD camera 145 may be acquired in a manner similar to the light acquisition system which acquires the data from the CCD camera 146 and then be stored for later use in the computer 150. The images may then be shown on a monitor (not shown) connected to the computer 150 and/or sent to a suitable printing device (not shown) connected to the computer 150.

Using the apparatus of the present invention, single cells in the living human retina have been routinely resolved for the first time. The adaptive optic system of the present invention provides a non-invasive technique with which to study the normal and pathological living retina at a microscopic spatial scale. The theoretical limit of the transverse resolution of fundus imaging is proportional to the diameter of the dilated pupil. If adaptive compensation were complete for an 8 mm pupil, for example, the transverse resolution would be increased 3.2 times over that for a 2.5 mm pupil, a typical pupil diameter used by currently available fundus cameras.

The axial resolution, which is critical in optical in-depth sectioning of the retina, grows as the square of the pupil diameter. Therefore, complete adaptive compensation across an 8 mm pupil could theoretically increase the axial resolution of a confocal ophthalmoscope by a factor of 10 over an instrument with a 2.5 mm exit pupil. The full-width at half-height (FWHH) of the PSF in depth is 27 microns, which approaches that of optical coherence tomography, but provides the additional advantage of high-transverse resolution not possible with optical coherence tomography alone.

The success of the apparatus of the present invention establishes that it can also be used to improve vision by reshaping the eye's optics, as in laser refractive surgery, or by fabricating customized optical elements such as contact lenses or intraocular lenses. As shown, FIGS. 1 and 2, the final correction signal can be provided to a contact lens or intraocular lens fabrication system or laser refractive surgical procedure 152 instead of the deformable mirror 118. As would be obvious to those of ordinary skill in the art, such contact lenses, intraocular lenses, or surgical correction would be customized for each eye for which compensation is to be provided. Additional aberrations besides defocus and astigmatism could be corrected with either an open or a closed loop system.

The invention described herein allows for the first complete description of the aberrations of the human eye combined with a demonstrated method to correct these aberrations. The applications of the present invention are four-fold. First, the invention can be utilized to provide a more accurate measure of the aberrations of the unaided eye. Second, the present invention can be used to evaluate the benefit of various techniques to correct the aberrations of the eye, such as custom glasses, custom contact lenses, and surgical procedures. Third, the present invention can be used to improve vision in optical instruments such as telescopes and binoculars, custom glasses, custom contact lenses, and with surgical procedures such as photorefractive keratectomy (PRK). Fourth, the invention can be utilized to improve the axial and transverse resolution of images of the living retina. Current fundus cameras suffer from the problem that, in the prior art, the aberrations of the eye limit its resolution, a limit that has remained since the invention of the ophthalmoscope.

Although only a preferred embodiment is specifically illustrated and described herein, it will be appreciated that many modifications and variations of the present invention are possible in light of the above teachings and within the purview of the appended claims without departing from the spirit and intended scope of the invention.

What is claimed is:

1. Apparatus for generating high resolution images of the retina of the living eye, comprising:
   means for generating a reflected point source image of the retina of said living eye;
   means for receiving said reflected point source image and for converting said point source image to corresponding digital signals;
   a digital data processor for calculating at least third order wave aberrations using said digital signals;
   means for illuminating said living eye for producing a retinal disk image;
   a compensating optical device for reflecting said retinal disk image, said compensating optical device being adjusted using said calculated wave aberrations such that wavefront compensation for said wave aberrations is provided for said living eye; and
   means for providing an image of said reflected retinal disk image after its reflection by said compensating optical device.

2. The apparatus of claim 1, wherein said compensating optical device is one of a deformable mirror, liquid crystal device, micro-machined mirror and bimorph mirror.

3. The apparatus of claim 1, wherein said means for generating comprises a plurality of lenslets which form a lenslet array for receiving said reflected point source image of said retina, said lenslet array being configured such that it is capable of providing resolution for at least third order aberrations.

4. The apparatus of claim 3, further including a polarizer through which said reflected point source image of said retina passes prior to being received by said plurality of lenslets.

5. Apparatus for generating high resolution images of the retina of the living eye, comprising:
   a first optical system for generating a reflected point source image of the retina of said living eye;
   a device for receiving said reflected point source image and for converting said point source image to corresponding digital signals;

a digital data processor for calculating said at least third order wave aberrations using said digital signals;

a second optical system for illuminating said living eye for producing a retinal disk image;

a compensating optical device for reflecting said retinal disk image, said compensating optical device being adjusted using said calculated wave aberrations such that wavefront compensation for said wave aberrations is provided for said living eye; and an imaging device for providing an image of said reflected retinal disk image after its reflection by said compensating optical device.

6. The apparatus of claim 5, wherein said compensating optical device is one of a deformable mirror, liquid crystal device, micro-machined mirror and bimorph mirror.

7. The apparatus of claim 5, wherein said wavefront sensor comprises a plurality of lenslets which form a lenslet array for receiving said reflected point source image of said retina, said lenslet array being configured such that it is capable of providing resolution for at least third order aberrations.

8. The apparatus of claim 7, further including a polarizer through which said reflected point source image of said retina passes prior to being received by said plurality of lenslets.

9. The apparatus of claim 5, wherein the second optical system illuminates a retinal disk on said living eye.

10. A method of generating a high resolution image of the retina of the living eye, comprising:

generating a reflected point source image of the retina of said living eye;

converting said point source image to corresponding digital signals;

calculating at least third order wave aberrations using said digital signals;

illuminating said living eye for producing a retinal disk image;

using a compensating optical device for reflecting said retinal disk image, said compensating optical device being adjusted using said calculated wave aberrations such that wavefront compensation for said wave aberrations is provided for said living eye; and providing an image of said reflected retinal disk image after its reflection by said compensating optical device.

* * * * *